(12) United States Patent
Nakanishi et al.

(10) Patent No.: US 9,616,170 B2
(45) Date of Patent: Apr. 11, 2017

(54) INFUSION PUMP

(71) Applicant: Terumo Kabushiki Kaisha, Tokyo (JP)

(72) Inventors: Masaru Nakanishi, Shizuoka (JP); Makoto Hasegawa, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 128 days.

(21) Appl. No.: 14/498,295

(22) Filed: Sep. 26, 2014

(65) Prior Publication Data
US 2015/0018766 A1 Jan. 15, 2015

Related U.S. Application Data

(63) Continuation of application No. PCT/JP2013/008282, filed on Dec. 25, 2012.

(30) Foreign Application Priority Data

Mar. 26, 2012 (JP) .................. 2012-069811

(51) Int. Cl.
*A61M 5/168* (2006.01)
*A61M 5/142* (2006.01)
(Continued)

(52) U.S. Cl.
CPC .... *A61M 5/16813* (2013.01); *A61M 5/14228* (2013.01); *A61M 39/281* (2013.01);
(Continued)

(58) Field of Classification Search
CPC .. A61M 5/14; A61M 5/1418; A61M 5/16804; A61M 2205/128; A61M 39/28;
(Continued)

(56) References Cited

U.S. PATENT DOCUMENTS 4,034,773 A * 7/1977 Huggins ............. A61M 39/285
137/1
5,389,071 A * 2/1995 Kawahara ............. A61M 5/172
128/DIG. 12

FOREIGN PATENT DOCUMENTS

JP 2004-166901 A 6/2004
JP 2006-141988 A 6/2006
(Continued)

OTHER PUBLICATIONS

Patent translate: translation of WO 2010023913 A1.*
Patent translate: translation of JP 2006141988 A.*
European Search Report dated Aug. 17, 2015 issued in EP12872575.

*Primary Examiner* — Bhisma Mehta
*Assistant Examiner* — Nilay Shah
(74) *Attorney, Agent, or Firm* — Foley & Lardner LLP

(57) ABSTRACT

An infusion pump comprises a tube attachment section configured such that an infusion tube is detachably attachable to the tube attachment section, an access cover configured to close the tube attachment section in an openable manner, and a tube clamp mechanism located within the tube attachment section and configured to clamp and block a portion of the infusion tube. The tube clamp mechanism comprises a base member, a clip clamp member rotatably mounted on the base member, a tube clamp release lever rotatably mounted on the base member, and a tube clamp member rotatably mounted on the base member.

16 Claims, 14 Drawing Sheets

(51) Int. Cl.
    *A61M 39/28* (2006.01)
    *A61M 5/14* (2006.01)
(52) U.S. Cl.
    CPC ............. *A61M 5/14* (2013.01); *A61M 5/1418* (2013.01); *A61M 5/16804* (2013.01); *A61M 39/28* (2013.01); *A61M 39/284* (2013.01); *A61M 2005/16863* (2013.01); *A61M 2005/16868* (2013.01); *A61M 2005/16872* (2013.01)
(58) Field of Classification Search
    CPC ............. A61M 39/284; A61M 39/286; A61M 39/285; A61M 5/16813; A61M 2005/16863; A61M 2005/16868; A61M 2005/16872; A61M 39/288
    See application file for complete search history.

(56) References Cited

FOREIGN PATENT DOCUMENTS

| | | | | | |
|---|---|---|---|---|---|
| JP | 2006141988 | A | * | 6/2006 | |
| JP | WO 2010023913 | A1 | * | 3/2010 | ........ A61M 5/14228 |
| JP | 2010-200775 | A | | 9/2010 | |

* cited by examiner

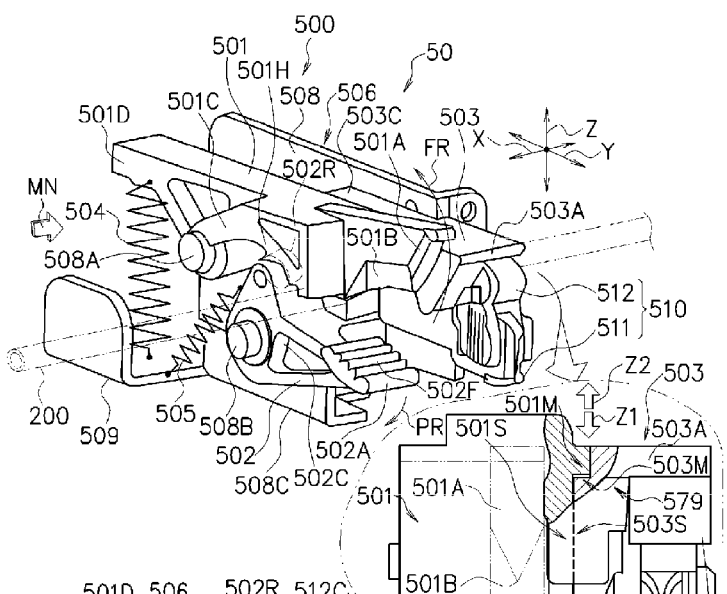
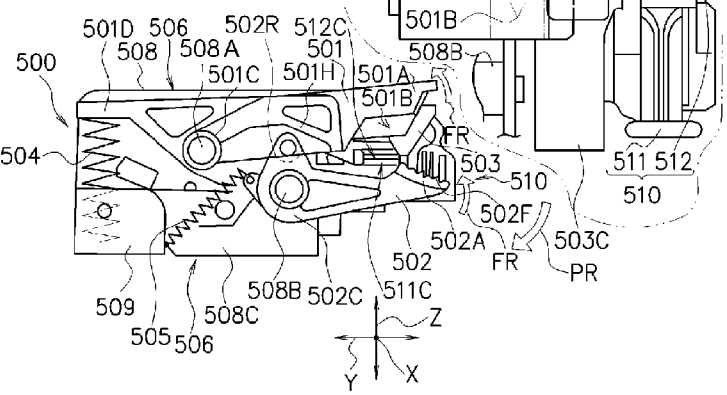

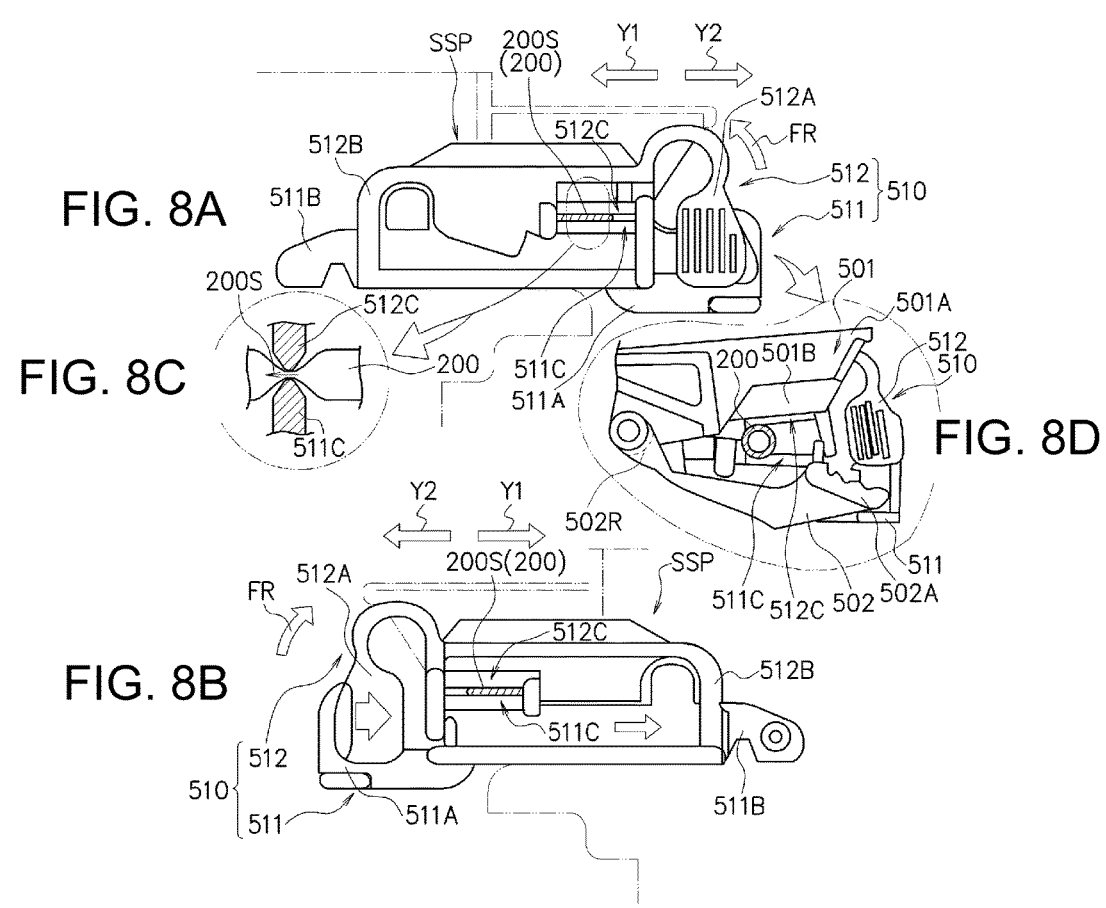

FIG. 9A
FIG. 9C
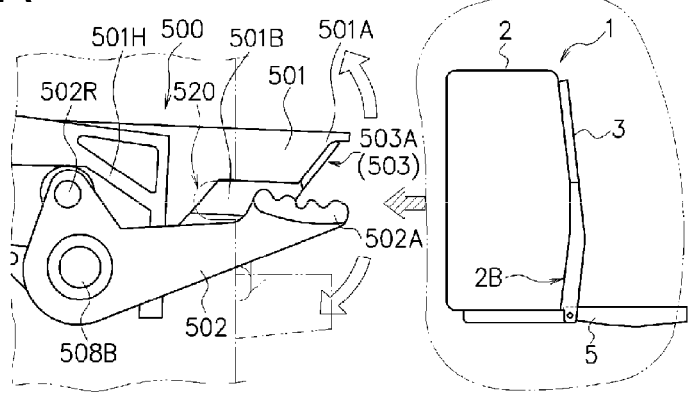
FIG. 9B
FIG. 9D
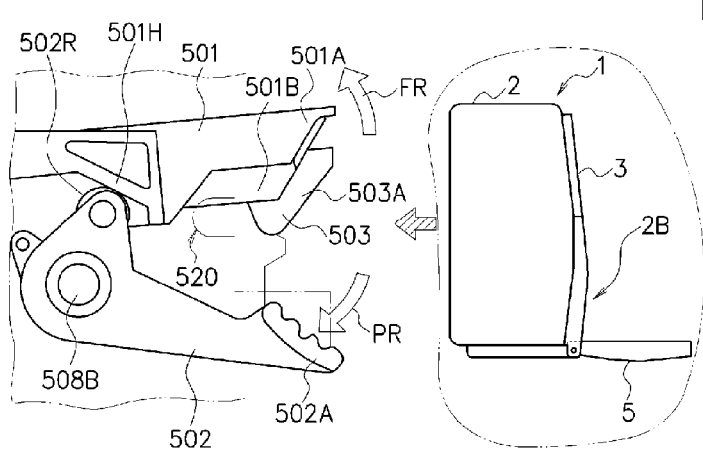

FIG.10
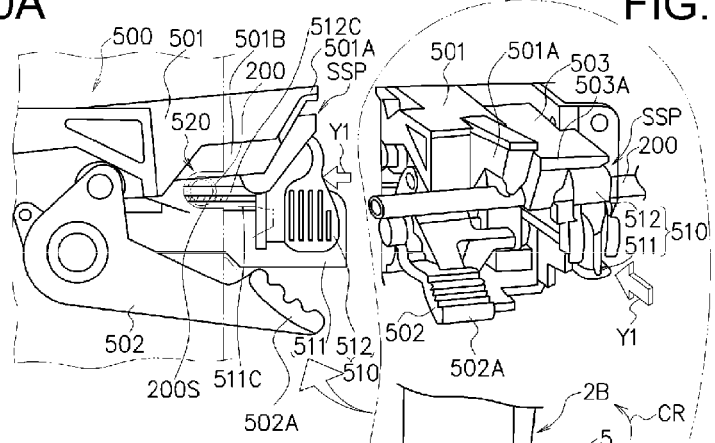
FIG. 10A
FIG. 10B
FIG. 10C
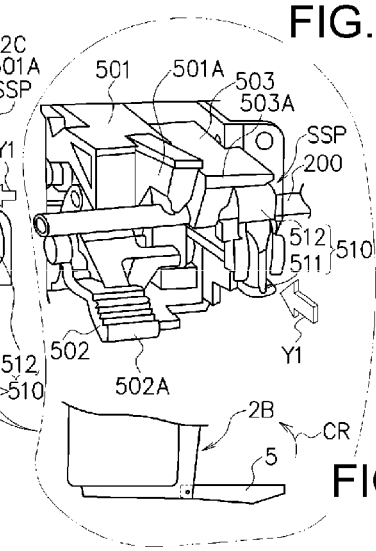
FIG. 10D
FIG. 10E
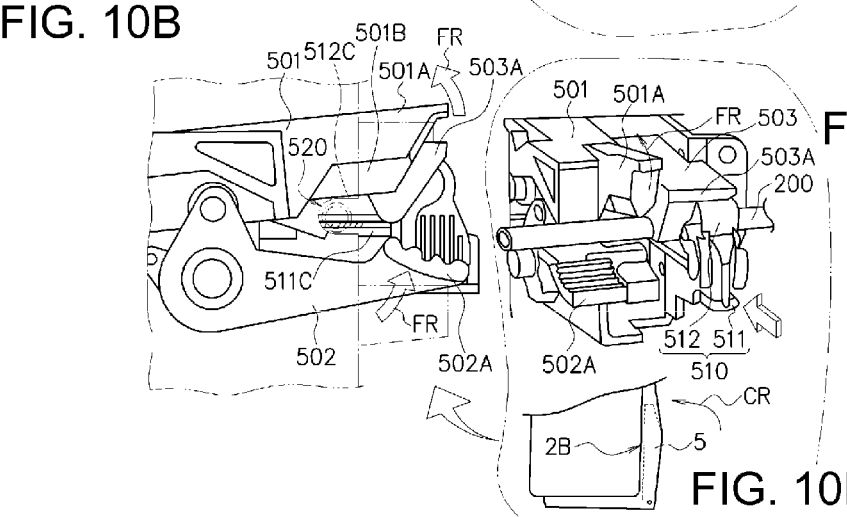
FIG. 10F

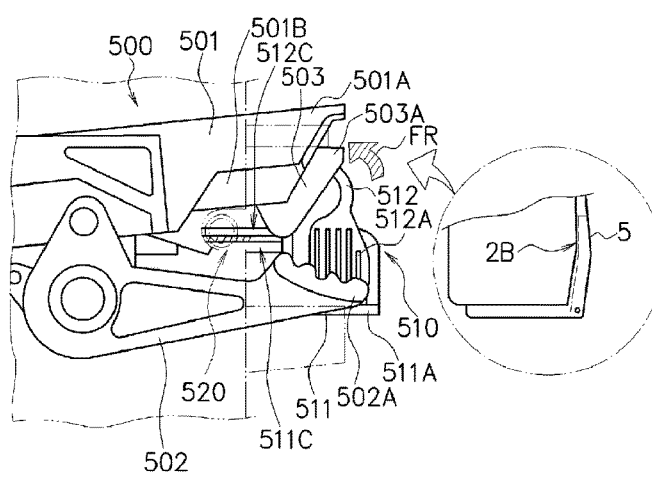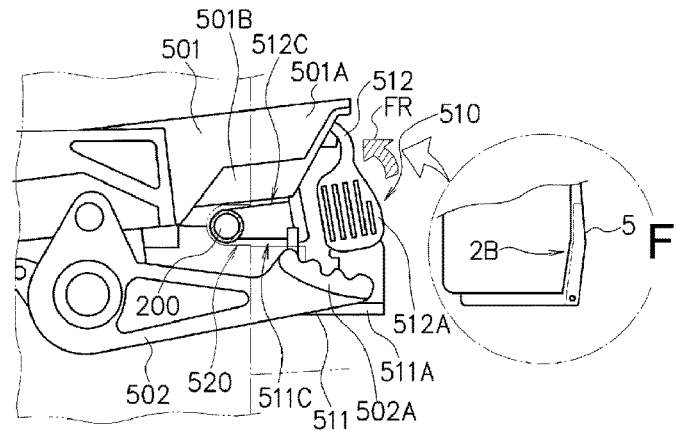

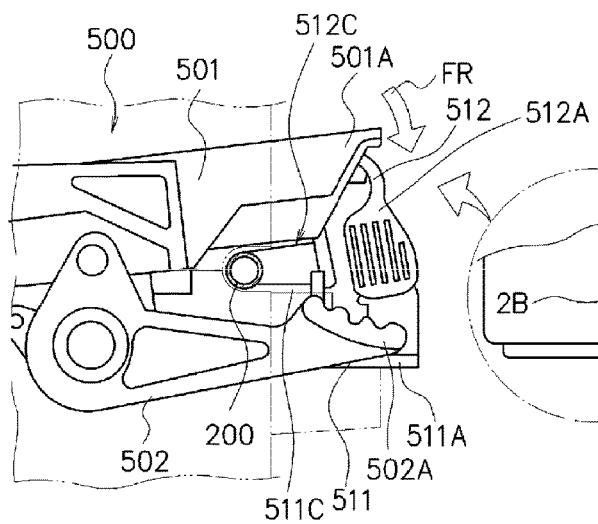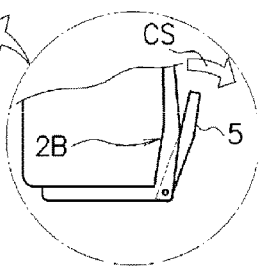

INFUSION PUMP

CROSS-REFERENCE TO RELATED APPLICATIONS

This application is a continuation application filed under 35 U.S.C. 111(a) claiming the benefit under 35 U.S.C. §§120 and 365(c) of PCT International Application No. PCT/JP2013/008282 filed on Dec. 25, 2012, which is based upon and claims the benefit of priority of Japanese Application No. 2012-069811 filed on Mar. 26, 2012, the entire contents of which are hereby incorporated by reference in their entireties.

BACKGROUND

Technical Field

The present disclosure relates to an infusion pump for feeding a medicine and the like to a patient.

Background Art

An infusion pump as an example of a medical pump is used in an intensive care unit (ICU) or the like, for example, and applied to feed a medicine to a patient for a relatively long period with high accuracy. The infusion pump includes a main body and an access cover. A predetermined medicine bag (infusion bag) is disposed above the infusion pump, and an infusion tube hung from the medicine bag is clipped between the main body and the access cover. The infusion tube is held by being housed inside the main body and closing the access cover. The infusion tube set at a predetermined position inside the main body of the infusion pump is clipped between a plurality of fingers inside the main body and an inner surface of the access cover. This infusion pump is a peristaltic infusion pump whereby the medicine is fed by individually driving the plurality of fingers at a liquid feed driving unit to cause the plurality of fingers to sequentially press an outer peripheral surface of the infusion tube along a length direction (see JP 2010-200775 A).

According to the infusion pump recited in the JP 2010-200775 A, the infusion tube is held being vertically passed through the inside of the main body of the infusion pump from above downward. In contrast, there is a proposed infusion pump whereby an infusion tube is held being horizontally passed through the inside of a main body of the infusion pump.

The configuration in which the infusion tube is thus held being horizontally passed through the inside of the main body of the infusion pump is adopted because a plurality of infusion pumps can be easily set, different from the infusion pump in which the infusion tube is vertically passed through the inside of the main body of the infusion pump from above downward. In other words, the configuration is adopted because there is a merit in which the infusion tube is not obstructive even though the plurality of infusion pumps is held being vertically stacked.

For instance, in the case where it is predetermined that an upstream side of the infusion tube is set at a right-side portion and a downstream side of the infusion tube is set at a left-side portion when a person faces the main body of the infusion pump, a medicine can be fed from the upstream side to the downstream side along the predetermined feeding direction and can be correctly fed to a patient by driving the liquid feed driving unit when the upstream side of the infusion tube is set at the right-side portion of the main body of the infusion pump and the downstream side of the infusion tube is set at the left-side portion of the main body of the infusion pump.

Meanwhile, in the case where the medicine freely flows through the infusion tube although the access cover is opened after the infusion tube is attached to the infusion pump, the medicine may be carelessly fed to a patient side through the infusion tube and an intravenous cannula and the medicine may be leaked out from the intravenous cannula of the infusion tube.

SUMMARY OF THE INVENTION

Considering the above, certain embodiments of the present invention are directed to provide an infusion pump capable of safely feeding medicinal solution, whereby a medicine is prevented from freely flowing through an infusion tube when the access cover is opened even though the infusion tube is attached to the infusion pump, and the medicinal solution is passed through the infusion tube when the access cover is closed.

An infusion pump according to certain embodiments of the present invention is configured to feed a medicine to a patient by using an infusion tube, and includes: a tube attachment section to which the infusion tube is detachably attached; an access cover that closes the tube attachment section in an openable manner; and a tube clamp mechanism provided at the tube attachment section and configured to clamp and block a middle portion of the infusion tube, wherein, in the case where the access cover is opened, a blocking portion is formed by a clip member at the infusion tube by closing the clip member preliminarily attached to the middle portion of the infusion tube, and in the case where the access cover is closed, the blocking portion formed at the infusion tube is eliminated by opening the clip member. The tube clamp mechanism includes: a base member; a clip clamp member rotatably mounted on the base member and configured to clamp the clip member, wherein, in the case where the access cover is opened, the blocking portion is formed at the infusion tube by closing the clip member; a tube clamp member rotatably mounted on the base member, wherein, in the case where the access cover is opened, the blocking portion is formed at the infusion tube by closing the clip member by pressing the clip clamp member, and in the case where the access cover is closed, the blocking portion formed at the infusion tube is eliminated by the access cover pushing the clip clamp member and releasing the clip clamp member from being pressed to open the clip member; and a tube clamp release lever rotatably mounted on the base member, wherein, when the tube clamp release lever is pushed by a user, the tube clamp member is pushed up in a direction away from the infusion tube to enable the clip clamp member to be pushed up, causing the clip member to be clamped by the clip clamp member.

According to the above-described configuration, the tube clamp mechanism provided at the tube attachment section is configured to form the blocking portion at the middle portion of the infusion tube by the clip member by closing the clip member preliminarily attached to the middle portion of the infusion tube in the case where the access cover is opened, and to eliminate the blocking portion formed at the tube by opening the clip member in the case where the access cover is closed. With this configuration, in the case where the access cover is still opened even after the infusion tube is attached to the infusion pump, the medicine is prevented from freely flowing through the infusion tube, and in the case where the access cover is closed, the medicinal solution can be passed through the infusion tube and the medicinal solution can be safely fed.

In one aspect, the blocking portion can be formed at the infusion tube by closing the clip member, if only provided with the tube clamp member, clip clamp member, and tube clamp release lever. Therefore, the medicine can be prevented from freely flowing through the infusion tube in the case where the access cover is still opened even though the infusion tube is attached to the infusion pump.

In one aspect, in the case where the access cover is opened when the clip member is not preliminarily attached to the middle portion of the infusion tube, the tube clamp member presses the middle portion of the infusion tube and forms the blocking portion, and in the case where the access cover is closed, the tube clamp member is separated from the infusion tube and eliminates the blocking portion.

In one aspect, even in the case where the user forgets attaching the clip member to the middle portion of the infusion tube when the clip member is not preliminarily attached to the middle portion of the infusion tube, the middle portion of the infusion tube is pressed to form the blocking portion in the case where the access cover is opened. Accordingly, in the case where the access cover is opened, the medicine can be prevented from freely flowing through the infusion tube.

In one aspect, an engagement section is provided, configured to engage the tube clamp member with the clip clamp member so as to be integrally rotated in a case of operating in a direction close to the to the infusion tube, and disengage the tube clamp member from the clip clamp member to release the clip clamp member from restriction of the tube clamp member in a case of operating in a direction away from the infusion tube.

In one aspect, the clip member can be easily attached and clamped to the clip clamp member because the engagement section disengages the tube clamp member from the clip clamp member and releases the clip clamp member from restriction of the tube clamp member when positioned in a direction away from the infusion tube.

In one aspect, a spring for biasing the tube clamp member toward the infusion tube is provided, and when the tube clamp release lever is pushed by the user, the tube clamp member is configured to be separated from the infusion tube against force of the spring.

In one aspect, when the tube clamp release lever is pushed by the user, the tube clamp member is separated from the infusion tube against force of the spring, thereby disengaging the tube clamp member from the clip clamp member and releasing the clip clamp member from restriction of the tube clamp member. Therefore, the clip member can be easily attached and clamped to the clip clamp member without being affected from the tube clamp member biased toward the infusion tube.

In one aspect, a display unit configured to display information and an operation panel having operating buttons are disposed on an upper portion of a main body of the infusion pump, and the tube attachment section and the access cover are disposed on a lower portion of the main body of the infusion pump.

In one aspect, a medical staff can feed the medicinal solution, confirming the information of the display unit at the upper portion of the main body, and also can operate the operating button on the operation panel, confirming the information of the display unit at the upper portion of the main body. The infusion tube can be attached by opening the access cover at the lower portion of the main body.

Certain embodiments of the present invention can provide an infusion pump capable of safely feeding the medicinal solution, whereby a medicine can be prevented from freely flowing in an infusion tube in the case where an access cover is opened even after the infusion tube is attached to the infusion pump, and medicinal solution can be passed through the infusion tube in the case where the access cover is closed.

BRIEF DESCRIPTION OF THE DRAWINGS

FIG. 7A is a left front perspective view illustrating an exemplary configuration of the tube clamp mechanism.

FIG. 7B is a side perspective view of the tube clamp mechanism in FIG. 7A viewed from a direction indicated by an arrow MN.

FIG. 7C is a front perspective view of the tube clamp mechanism shown in FIGS. 7A and 7B.

FIG. 8A is a diagram illustrating a left side surface of a clip member (downstream side surface).

FIG. 8B is a diagram illustrating a right side surface of the clip member (upstream side surface).

FIG. 8C is a close up view showing the infusion tube of FIG. 8A from a front perspective view.

FIG. 8D is a left perspective view of the tube clamp mechanism.

FIG. 9A is a diagram illustrating a state in which the access cover is opened.

FIG. 9B is a diagram illustrating the mechanism of FIG. 9A after a tube clamp member is pushed and expanded upward by pressing down a tube clamp release lever of the tube clamp mechanism.

FIG. 9C. is a diagram illustrating the position of the access cover related to the position of the mechanism in FIG. 9A.

FIG. 9D. is a diagram illustrating the position of the access cover related to the position of the mechanism in FIG. 9B.

FIG. 10A is a diagram illustrating a state in which a medicine is inhibited from passing through the infusion tube by forming a blocking portion at the infusion tube when the clip member preliminarily attached to the infusion tube is inserted into the tube clamp mechanism.

FIG. 10B is a diagram illustrating a later state than that of FIG. 10A in which the tube clamp member is lifted up by closing the access cover.

FIG. 10C is a front left perspective view of the state shown in FIG. 10A.

FIG. 10D. is a diagram illustrating the position of the access cover related to the position of the mechanism in FIGS. 10A and 10C.

FIG. 10E is a front left perspective view of the state shown in FIG. 10B.

FIG. 10F. is a diagram illustrating the position of the access cover related to the position of the mechanism in FIGS. 10B and 10E.

FIG. 11A is a diagram illustrating a state in which a clip clamp member is lifted up together with the tube clamp member being lifted up.

FIG. 11B is a diagram illustrating a state in which the blocking portion at the infusion tube is eliminated and the medicinal solution passes through the infusion tube by opening the clip member with the clip member's own elastic force to release the infusion tube from being pressured.

FIG. 11C is a diagram illustrating the position of the access cover related to the position of the mechanism in FIG. 11A.

FIG. 11D is a diagram illustrating the position of the access cover related to the position of the mechanism in FIG. 11B.

FIG. 12A is a diagram illustrating a state in which the clip member is going to be closed when the access cover is going to be opened.

FIG. 12B is a diagram illustrating the position of the access cover related to the position of the mechanism in FIG. 12A.

DETAILED DESCRIPTION

In the following, a preferred embodiment of the present invention will be described in detail with reference to accompanying drawings.

Note that the embodiment described below contains various technical preferred limitations because a preferable case according to the present invention where an infusion tube is horizontally attached to an infusion pump is exemplified, but a technical scope of the present invention is not limited thereto unless otherwise particularly specified for limiting the present invention in the following description.

Figure 1:
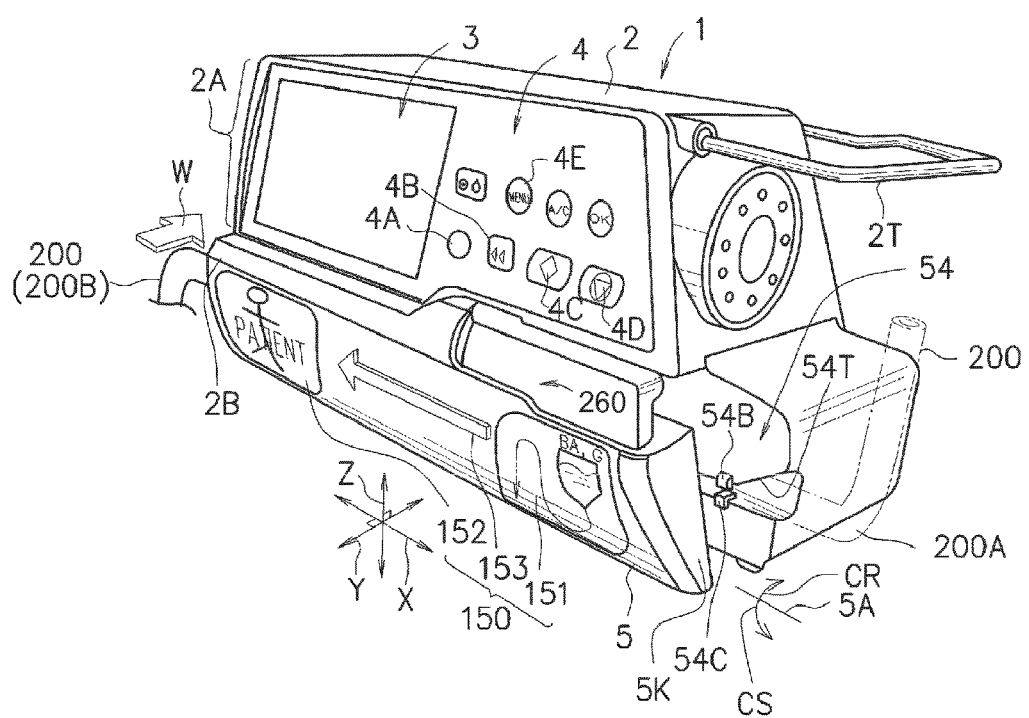
FIG. 1 is a perspective view illustrating a preferred embodiment of an infusion pump according to an embodiment of the present invention.
Figure 2:
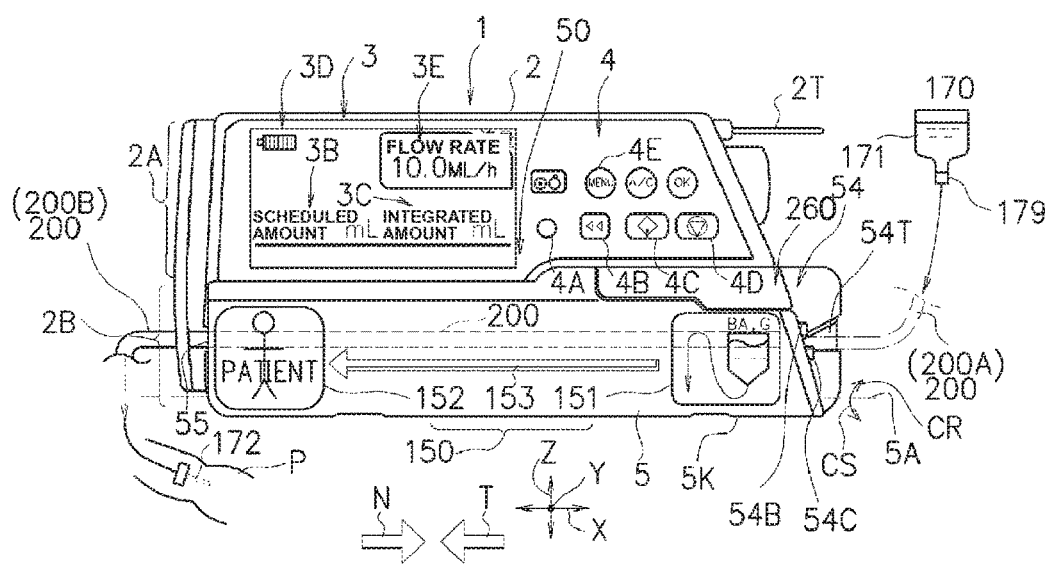
FIG. 2 is a front view of the infusion pump illustrated in FIG. 1 viewed from a W-direction.

FIG. 1 is a perspective view illustrating a preferred embodiment of an infusion pump according to an embodiment of the present invention. FIG. 2 is a front view of the infusion pump illustrated in FIG. 1 viewed from a W-direction.

Figure 3:
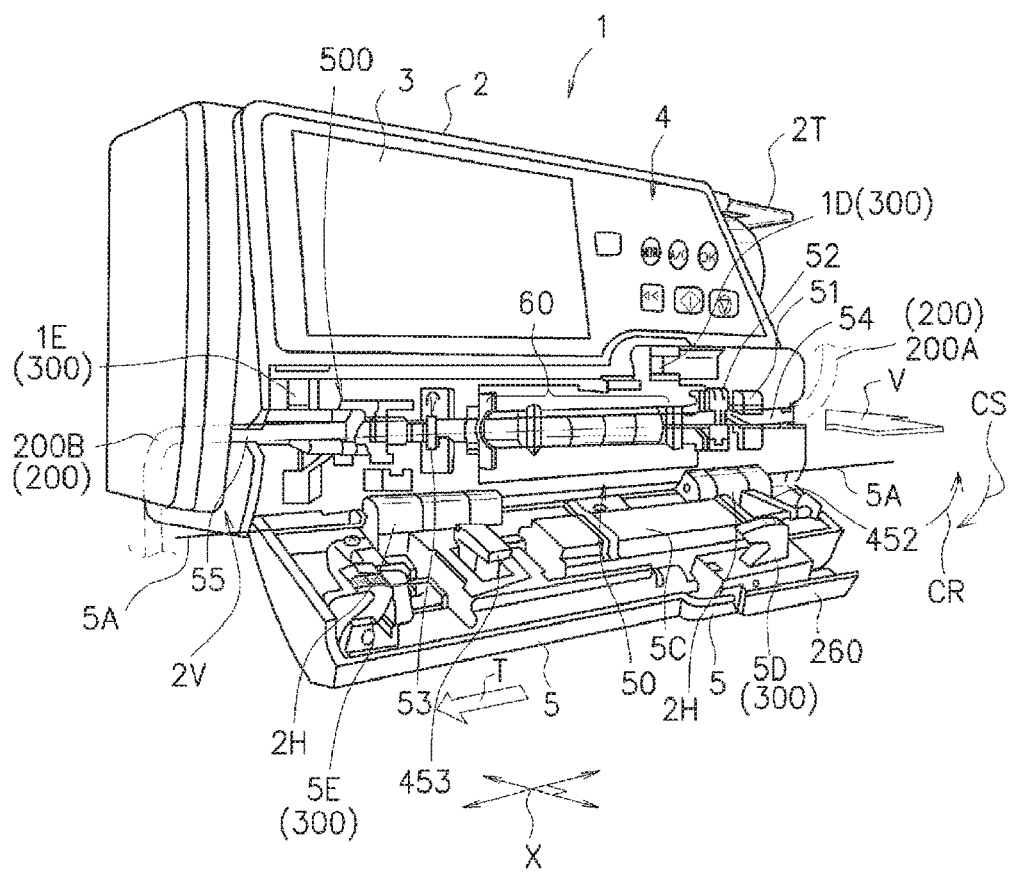
FIG. 3 is a perspective view illustrating a state in which a tube attachment section to which an infusion tube is to be attached and the infusion tube are exposed by opening an access cover of the infusion pump illustrated in FIGS. 1 and 2.
Figure 4:
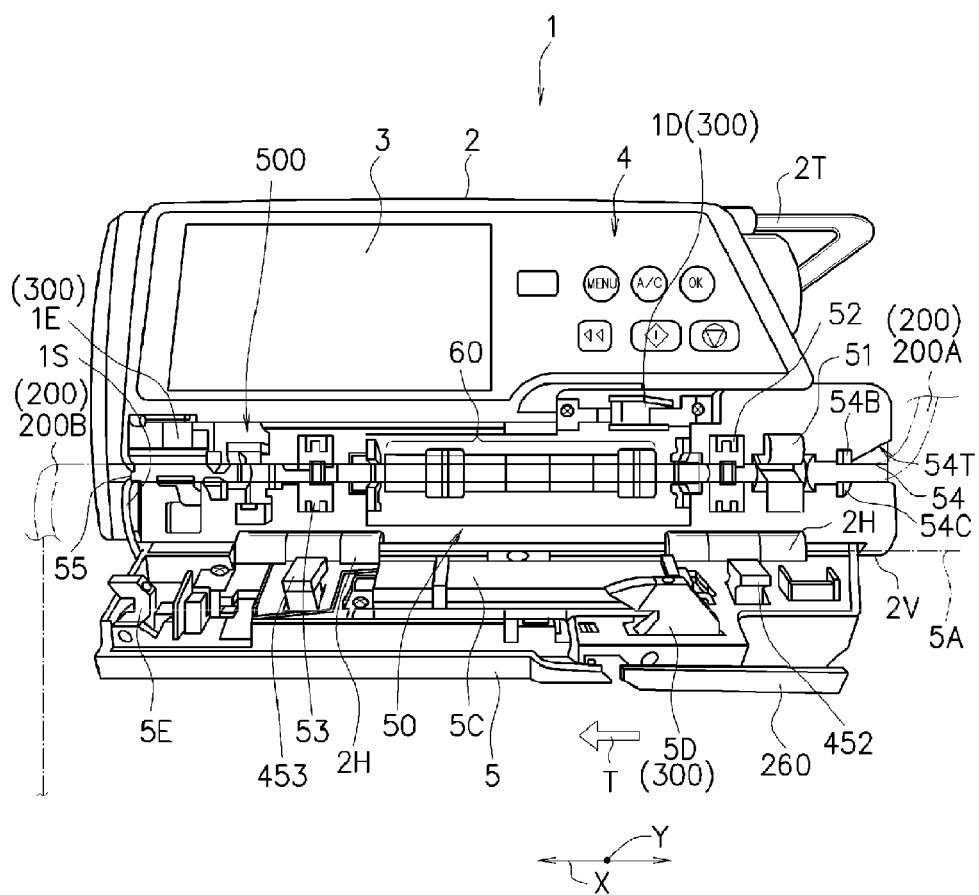
FIG. 4 is a front view of the infusion pump illustrated in FIG. 3 viewed from a V-direction.

FIG. 3 is a perspective view illustrating a state in which an access cover 5 of an infusion pump 1 illustrated in FIGS. 1 and 2 is opened, and a tube attachment section 50 where an infusion tube 200 is attached and the infusion tube 200 are exposed. FIG. 4 is a front view of the infusion pump 1 illustrated in FIG. 3 viewed from a V-direction.

The infusion pump 1 illustrated in FIGS. 1 and 2 is used in an intensive care unit (ICU, CCU, NICU) and the like, and is an injection pump used for injecting medicines, such as anticancer drugs, anesthetics, chemotherapeutic agents, blood to be transfused, and nutritional supplements, to a patient with high accuracy for a relatively long time.

A medicine is selected from a medicine library, for example, and the infusion pump 1 is used to feed the selected medicine. The medicine library is information of medicines corresponding to medicine administering setting groups including names of medicines preliminarily registered in a medicine library database (DB). A medical staff can select a medicine and set the medicine by using the medicine library without executing complicated setting for medicine administration in each case.

As illustrated in FIG. 2, the infusion pump 1 correctly feeds a medicine 171 to a patient P from a medicine bag 170 filled with the medicine 171 through a forceps 179, an infusion tube 200, and an intravenous cannula 172. The infusion pump 1 includes a main body 2 and a handle 2T. The main body 2 is also called a main body case which is integrally formed of a molded resin material having chemical resistance, and is provided with a splash proof structure whereby a medicine or the like can be prevented from entering the inside of the infusion pump 1 even when the medicine or the like is splashed. The main body 2 is thus provided with the splash proof structure because there is possibility that medicine 171 contained in the medicine bag 170 disposed above spills down, or disinfectant or the like used nearby splashes and adheres.

First, elements disposed at the main body 2 of the infusion pump 1 will be described. As illustrated in FIGS. 1 and 2, a display unit 3 and an operation panel 4 are disposed at an upper portion 2A of the main body 2. The display unit 3 is an image display unit, for example, using a display unit formed of a color LCD and an organic EL. The display unit 3 is positioned at the upper left of the upper portion 2A of the main body 2 and is disposed on an upper side of an access cover 5. The upper portion 2A of the main body 2 is an upper half of the main body 2. A lower portion 2B of the main body 2 is a lower half of the main body 2.

In FIG. 2, the display unit 3 displays, as an example, a scheduled amount of medicine administration (mL) at a display field 3B, an integrated amount of medicine administration (mL) at a display field 3C, a charge history at a display field 3D, and a flow rate (mL) at a display field 3E, but the display unit 3 illustrated in FIG. 1 omits these display contents for simplifying the drawing. The display unit 3 also can display a warning message besides the above-mentioned information.

As illustrated in FIG. 1, the operation panel 4 is disposed on a right side of the display unit 3 at the upper portion 2A of the main body 2, and for example, a pilot lamp 4A, a fast feeding switch button 4B, a start switch button 4C, a stop switch button 4D, a menu select button 4E, etc. are provided at the operation panel 4. A power switch button is provided at a position different from the operation panel 4.

As illustrated in FIG. 1, the access cover 5 as a cover member can be opened in a CS-direction and closed in a CR-direction centering a rotary shaft 5A at the lower portion 2B of the main body 2. The access cover 5 can be also called an access door or an opening/closing door. The access cover 5 can cover the tube attachment section 50 at the lower portion 2B when closed, and can expose the tube attachment section 50 and the infusion tube 200 when opened.

The infusion tube 200 made of a flexible thermoplastic resin such as flexible polyvinyl chloride or the like can be detachably attached to the tube attachment section 50 at the lower portion 2B illustrated in FIG. 3. The infusion tube 200 is a pipe line member having a circular cross section and elastically deformable. Therefore, even in the case of being pressed, the infusion tube returns to an original shape when released from pressing force. The access cover 5 rotates in the CR-direction and closes the tube attachment section 50, thereby the access cover 5 holding the infusion tube 200 at the tube attachment section 50, particularly preferably, horizontally along the X-direction.

As illustrated in FIG. 2, a feeding direction display unit 153 is provided to clearly indicate a correct feeding direction T of the medicine 171 executed by the infusion tube 200 set inside the access cover 5, and indicates an arrow directed from a medicine bag display unit 151 to a display unit 152 on the patient side along the T-direction. A setting direction display unit 150 of the infusion tube may be pasted on a front surface side of the access cover 5 afterwards. Note that the X-direction, a Y-direction, and a Z-direction in FIGS. 1 and 2 are orthogonal to one another, and the Z-direction is a vertical direction. The X-direction is parallel to the feeding direction T corresponding to the horizontal direction of the infusion pump 1, and the Y-direction is a front-back direction of the infusion pump 1.

As illustrated in FIGS. 3 and 4, the tube attachment section 50 is provided on the side of the lower portion 2B of the main body 2 of the infusion pump 1, and the tube attachment section 50 is disposed at a lower portion of the display unit 3 and the operation panel 4 along the X-direction. As illustrated in FIG. 2, the tube attachment section 50 can be covered by the access cover 5 when the access cover 5 is closed in the CR-direction, centering the rotary shaft 5A, and the tube attachment section 50 can be exposed when the access cover 5 is opened in the CS-direction, centering the rotary shaft 5A.

The medical staff, namely, a user can attach the infusion tube 200 to the tube attachment section 50, confirming the information of the display unit 3 at the upper portion 2A of the main body 2, and can close the access cover 5. Further, the medical staff can operate the operating button at the operation panel 4, confirming the information of the display unit 3 at the upper portion 2A of the main body 2.

As illustrated in FIGS. 3 and 4, the tube attachment section 50 includes a bubble sensor 51, an upstream block sensor 52, a downstream block sensor 53, a first infusion tube holding unit 54 at a right-side position, and a second infusion tube holding unit 55 at a left-side position.

The tube clamp mechanism 500 later described is provided at the left-side position of the tube attachment section 50. The tube clamp mechanism 500 is disposed between the downstream block sensor 53 and the second infusion tube holding unit 55.

Now, an exemplary configuration of the access cover 5 illustrated in FIGS. 3 and 4 will be described. As illustrated in FIGS. 3 and 4, the access cover 5 is mounted on a lower portion 2V of the main body 2 by two hinges 2H so as to cover the tube attachment section 50 in an openable manner centering the rotary shaft 5A along the CS-direction and CR-direction. The two hinges 2H are provided corresponding to a hook member 5D and a hook member 5E, respectively.

As illustrated in FIGS. 2 and 3, an open/close operation lever 260 is provided at an upper right portion on the front surface side of the access cover 5. As illustrated in FIGS. 3 and 4, an infusion tube pressing member 5C, the hook member 5D, and the hook member 5E are provided on an inner surface side of the access cover 5. This infusion tube pressing member 5C is disposed as a protrusion shaped in a long rectangular plane formed along the X-direction, and positioned facing a liquid feed driving unit 60 on the side of the main body 2. The infusion tube pressing member 5C is a flat surface in the X-direction along the liquid feed driving unit 60. By closing the access cover 5 in the CR-direction, the infusion tube pressing member 5C is configured to press and clip a part of the infusion tube 200 with the liquid feed driving unit 60. With this configuration, an outer peripheral surface of the infusion tube 200 is sequentially pressed by a plurality of fingers along a length direction by individually driving the plurality of fingers (not illustrated) of the liquid feed driving unit 60, thereby achieving to feed the medicine inside the infusion tube 200 in the T-direction.

As illustrated in FIGS. 3 and 4, the two hook members 5D, 5E are positioned facing fixing portions 1D, 1E, respectively on the side of the lower portion 2B of the main body 2. The two hook members 5D, 5E are mechanically hooked on the respective fixing portions 1D, 1E on the side of the lower portion 2B of the main body 2 at the same time, thereby achieving to hold the access cover 5 covering the tube attachment section 50 at the lower portion 2B of the main body 2 as illustrated in FIG. 2. The two hook members 5D, 5E and fixing portions 1D, 1E on the side of the lower portion 2B of the main body 2 form a double hook structure 300 of the access cover 5.

As illustrated in FIG. 4, in the tube attachment section 50, the liquid feed driving unit 60, downstream block sensor 53, and tube clamp mechanism 500 are disposed between the hook member 5D and hook member 5E. However, in the tube attachment section 50, the bubble sensor 51 and upstream block sensor 52 are disposed at positions to the right of the hook member 5D.

The medical staff, namely the user, can set the infusion tube 200 to the tube attachment section 50 along the horizontal direction, confirming the indicated contents displayed on the display unit 3, and then closes the access cover 5 to cover the tube attachment section 50 and the infusion tube 200. As illustrated in FIGS. 3 and 4, when the infusion tube 200 is horizontally set in the X-direction, the infusion tube 200 is set so as to pass through the tube clamp mechanism 500.

As illustrated in FIG. 4, the first infusion tube holding unit 54 is disposed at the right-side portion of the lower portion 2B of the main body 2 and the second infusion tube holding unit 55 is disposed at the left-side portion of the lower portion 2B of the main body 2 when a person faces the main body. The first infusion tube holding unit 54 is configured to receive an upstream side 200A of the infusion tube 200, and the second infusion tube holding unit 55 is configured to receive a downstream side 200B of the infusion tube 200, thereby configured to horizontally hold the infusion tube 200 along the X-direction. Thus, the infusion tube 200 horizontally held is disposed along the bubble sensor 51, upstream block sensor 52, liquid feed driving unit 60, downstream block sensor 53, and tube clamp mechanism 500.

As illustrated in FIG. 4, the first infusion tube holding unit 54 preferably includes two protrusions 54B, 54C and a slanted guide portion 54T. The two protrusions 54B, 54C detachably clip and hold the upstream side 200A of the infusion tube 200 at the time of horizontally setting the infusion tube 200. The slanted guide portion 54T is a portion formed in an oblique upper-right direction from the two protrusions 54B, 54C so as to obliquely guide the upstream side 200A of the infusion tube 200. As illustrated in FIGS. 1 and 2, a right side surface portion 5K of the access cover 5 is formed slanted in an oblique upper-left direction.

With this configuration, the access cover 5 is configured not to cover the two protrusions 54B, 54C and the slanted guide portion 54T of the first infusion tube holding unit 54 even when the access cover 5 is closed. Also, the medical staff can visually check an attaching state of the upstream side 200A of the infusion tube 200 by constantly exposing the two protrusions 54B, 54C and the slanted guide portion 54T even when the access cover 5 is closed.

By providing the slanted guide portion 54T, the medical staff can visually check that the upstream side 200A of the infusion tube 200 is set on the side of the slanted guide portion 54T, and also the upstream side 200A of the infusion tube 200 can be held without being rapidly bent.

The second infusion tube holding unit 55 illustrated in FIG. 4 is a groove configured to hold the downstream side 200B of the infusion tube 200 by detachably clipping a part thereof, and formed at a side surface portion 1S of the lower portion 2B of the main body 2. The first infusion tube holding unit 54 and second infusion tube holding unit 55 illustrated in FIG. 4 can surely attach the infusion tube 200 to the inside of the tube attachment section 50 without damaging the infusion tube 200 by clipping the infusion tube between the access cover 5 and the tube attachment section 50.

The bubble sensor 51 illustrated in FIG. 4 detects bubbles (air) generated inside the infusion tube 200, and for example, the bubble sensor 51 is an ultrasonic sensor that monitors the bubbles contained inside the medicine flowing inside the infusion tube 200 from the outside of the infusion tube 200 such as flexible polyvinyl chloride. Since transmissivity of the ultrasonic in the medicine differs from the transmissivity of the ultrasonic in the bubbles, a receiving unit of the ultrasonic sensor detects a difference of the transmissivity to monitor presence of the bubbles by applying the ultrasonic generated from a transmitting unit of the ultrasonic sensor to the medicine flowing inside the infusion tube 200.

Referring to FIG. 4, the upstream block sensor 52 is a sensor that detects whether the inside of the infusion tube 200 is blocked at the upstream side 200A of the infusion tube 200, and the downstream block sensor 53 is a sensor that detects whether the inside of the infusion tube 200 is blocked at the downstream side 200B of the infusion tube 200. The upstream block sensor 52 and downstream block sensor 53 have the same configuration. The cases where the infusion tube 200 is blocked are, for example, when the infusion tube 200 is bent in the middle and kinked, or when a needle tip is blocked by a blood clot.

As illustrated in FIG. 4, pressing members 452, 453 are respectively provided on the inner surface side of the access cover 5 at positions corresponding to the upstream block sensor 52 and the downstream block sensor 53. With this configuration, when the medical staff closes the access cover 5 as illustrated in FIG. 2 after setting the infusion tube 200 at the tube attachment section 50 as illustrated in FIG. 3, the pressing member 452 and pressing member 453 provided on the side of the access cover 5 can press a part of the infusion tube 200 against the upstream block sensor 52 side and the downstream block sensor 53 side, respectively.

Figure 5:
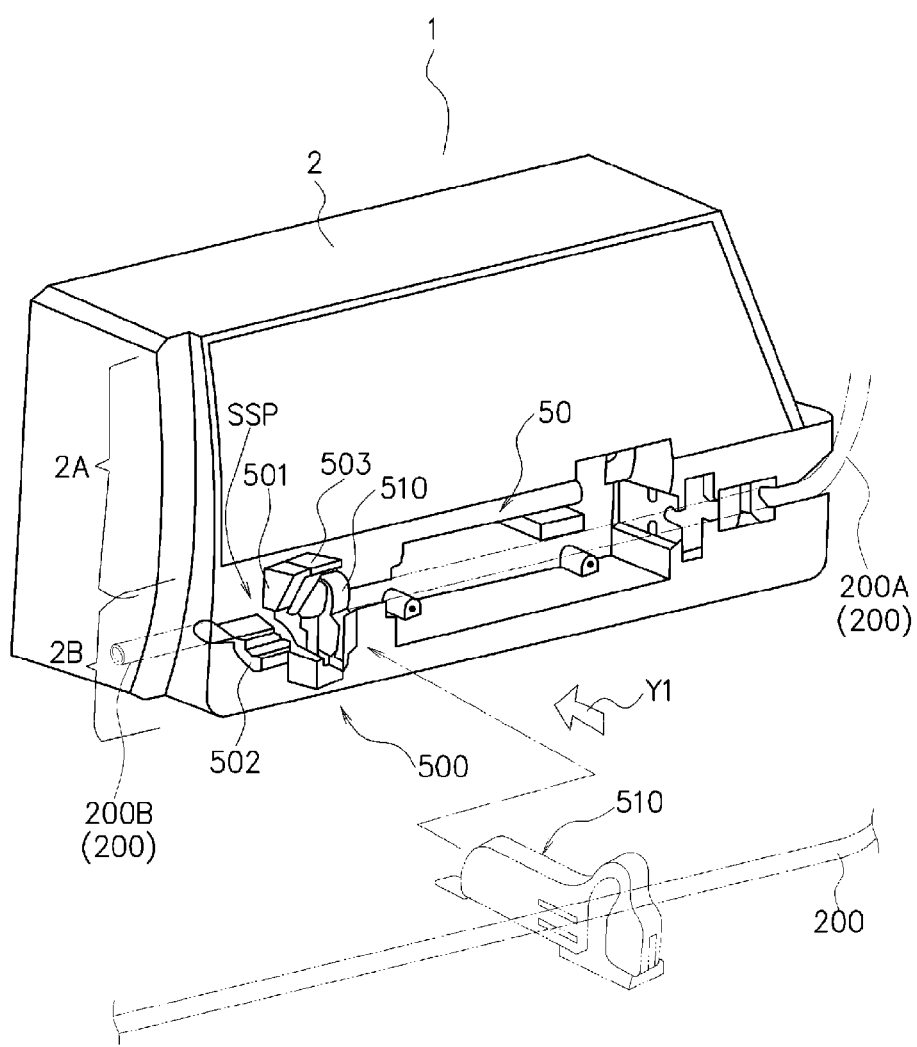
FIG. 5 is a perspective view of a main body illustrated in FIG. 1.
Figure 6A:
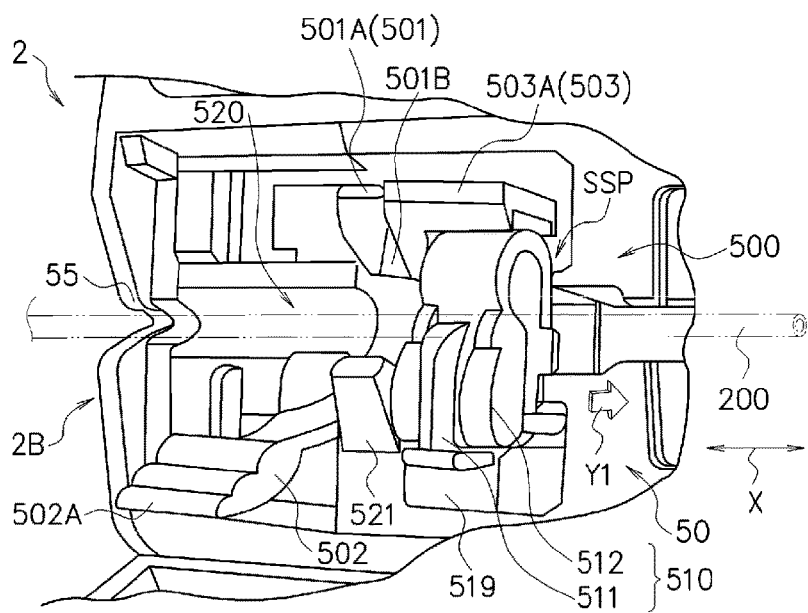
FIG. 6A is an enlarged perspective view illustrating the vicinity of a tube clamp mechanism at a lower portion of the main body illustrated in FIG. 5
Figure 6B:
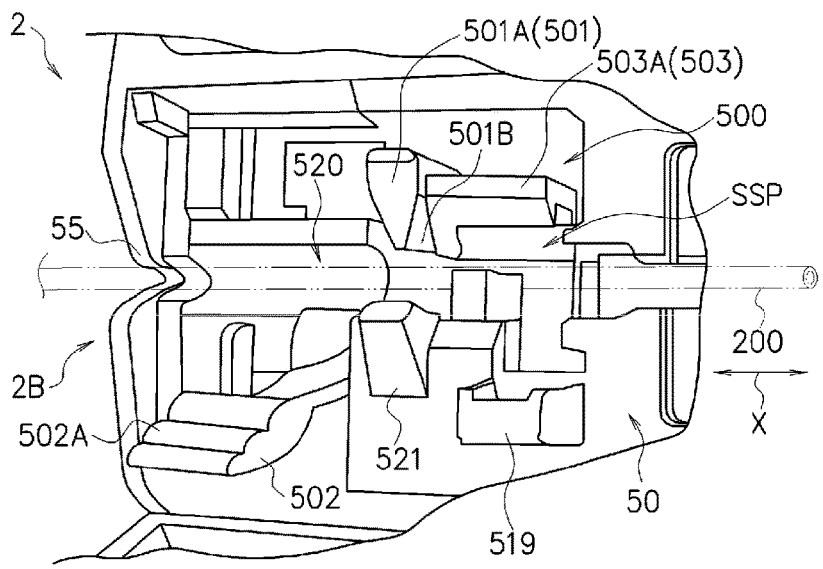
FIG. 6B is an enlarged perspective view illustrating the vicinity of a tube clamp mechanism at a lower portion of the main body illustrated in FIG. 5 shown without a clip member.

FIG. 5 is a perspective view of a main body 2 illustrated in FIG. 1. The tube attachment section 50 at the lower portion 2B of the main body 2 is provided with the tube clamp mechanism 500. FIGS. 6A and 6B are enlarged perspective views illustrating the vicinity of the tube clamp mechanism 500 of the main body 2 illustrated in FIG. 5. FIG. 7A is a perspective view illustrating an exemplary configuration of the tube clamp mechanism 500, and FIG. 7B is a side view of the tube clamp mechanism 500 in FIG. 7A viewed from a direction indicated by an arrow MN.

As illustrated in FIG. 3, in the case where the access cover 5 is opened although the infusion tube 200 has been set to the tube attachment section 50 of the infusion pump 1 in the X-direction (horizontal direction), the tube clamp mechanism 500 inhibits the medicine 171 illustrated in FIG. 2 from freely flowing through the infusion tube 200 along the T-direction. Further, as illustrated in FIG. 2, in the case where the infusion tube 200 has been set to the tube attachment section 50 of the infusion pump 1 in the X-direction (horizontal direction) and the access cover 5 is closed, the tube clamp mechanism 500 is configured to feed the medicine 171 in the T-direction through the infusion tube 200.

Now, an exemplary configuration of the tube clamp mechanism 500 will be described with reference to FIGS. 7A and 7B. As illustrated in FIGS. 7A and 7B, the tube clamp mechanism 500 includes a tube clamp member 501, a tube clamp release lever 502, a clip clamp member 503, a first spring 504 for biasing the tube clamp member 501, a second spring 505 for biasing the tube clamp release lever 502, and a base member 506 made of metal. The base member 506 is fixed along the Z-direction inside the tube attachment section 50.

Further, a spring constant (kgf/mm) of the second spring 505 is 3 to 8 percent of the spring constant (kgf/mm) of the first spring 504, preferably, 4 to 6 percent, and more preferably, 5 percent. Note that, preferably, a torsion coil spring is used for both the first spring 504 and the second spring 505.

The tube clamp mechanism 500 in FIGS. 7A and 7B is disposed at a recessed portion provided at the tube attachment section 50 illustrated in FIGS. 6A and 6B. The base member 506 is fixed to a wall portion of the recessed portion at the tube attachment section 50 by using a screw. An attachment space SSP is provided at a lower portion of the clip clamp member 503. The attachment space SSP is a space preliminarily prepared for detachably inserting and attaching a later-described clip member 510 illustrated in FIG. 5. The tube clamp member 501 and the tube clamp release lever 502 are disposed at the more downstream side in the T-direction, namely, the flowing direction of the medicinal solution inside the infusion tube 200, compared to the clip clamp member 503 and the attachment space SSP. In other words, the clip clamp member 503 and the space SSP are disposed at the more upstream in the T-direction, compared to the tube clamp member 501 and the tube clamp release lever 502. With this configuration, the medical staff can easily attach the clip member 510 inside the attachment space SSP located on the right side of the tube clamp release lever 502 by pinching and holding the clip member 510 with the right hand fingers.

The tube clamp member 501, tube clamp release lever 502, and clip clamp member 503 illustrated in FIGS. 7A and 7B are respectively plastic products. The first spring 504 and the second spring 505 are, for example, metal-made coil springs.

FIGS. 6A, 7A and 7B are the views illustrating a state in which the clip member 510 is detachably attached inside the attachment space SSP of the tube clamp mechanism 500. The clip member 510 is formed of a plastic member as described later. The clip member 510 detachably clips a middle portion of the infusion tube 200, thereby forming a blocking portion by squeezing the middle portion of the infusion tube 200.

In the state illustrated in FIGS. 6A, 7A and 7B, the clip member 510 is preliminarily attached to the middle portion of the infusion tube 200, and the clip member 510 is detachably attached inside the attachment space SSP of the tube clamp mechanism 500. Accordingly, the clip member 510 is configured to block the middle portion of the infusion tube 200.

However, in the state illustrated in FIG. 6B, the clip member 510 is not preliminarily attached to the middle portion of the infusion tube 200, and the clip member 510 is not preliminarily attached to the tube clamp mechanism 500. In other words, this is a case where the medical staff forgets to preliminarily attach the clip member 510 to the middle portion of the infusion tube 200, for example, and this is why the clip member 510 is not preliminarily attached to the middle portion of the infusion tube 200.

A configuration of the base member 506 of the tube clamp mechanism 500 illustrated in FIGS. 7A and 7B will be described.

The base member 506 illustrated in FIGS. 7A and 7B includes a main body 508, an extending portion 509, and a side portion 508C. The main body 508 and the side portion 508C are plates formed in the Z-direction. The main body 508 includes a shaft portion 508A, and the side portion 508C includes a shaft portion 508B. The shaft portions 508A, 508B are formed in a protruding manner from one surface of the main body 508 and one surface of the side portion 508C, parallel to the X-direction, and respectively apart. The extending portion 509 is formed in a protruding manner from the main body 508 in the X-direction.

A configuration of the tube clamp member 501 illustrated in FIGS. 7A and 7B will be described. As illustrated in FIGS. 7A and 7B, the tube clamp member 501 includes an operation end portion 501A, a tube blocking section 501B, a supporting portion 501C, and a rear end portion 501D. The first spring 504 is mounted between the rear end portion 501D of the tube clamp member 501 and the extending portion 509. The supporting portion 501C is a tubular portion where the shaft portion 508A is passed through, and formed between the operation end portion 501A and the rear end portion 501D. With this configuration, the operation end portion 501A can be rotated in the FR-direction (Z2 direction) around the supporting portion 501C against force of the first spring 504. The tube blocking section 501B is formed to be gradually sharp along the Z1 direction toward, and configured to form the blocking portion by squeezing the middle portion of the infusion tube 200.

Next, a configuration of the tube clamp release lever 502 illustrated in FIGS. 7A and 7B will be described. As illustrated in FIGS. 7A and 7B, a tube clamp release lever 502 includes an operation end portion 502A, a supporting portion 502C, and a roller 502R. The tube clamp release lever 502 is disposed at the lower portion of the tube clamp member 501. The operation end portion 502A is one end portion of the tube clamp release lever 502, and the supporting portion 502C is the other end portion of the tube clamp release lever 502. The supporting portion 502C is a tubular portion where the shaft portion 508B is passed through. The operation end portion 502A of the tube clamp release lever 502 includes a wave-shaped portion 502F. The medical staff can push down the wave-shaped portion 502F by the fingers in a PR-direction (Z1-direction) centering the supporting portion 502C.

The second spring 505 is mounted between the supporting portion 502C and the extending portion 509 illustrated in FIGS. 7A and 7B. The second spring 505 exerts force to push up the operation end portion 502A of the tube clamp release lever 502 in the FR-direction. Further, the roller 502R is mounted at an upper portion of the supporting portion 502C.

With this configuration, when the medical staff pushes down the operation end portion 502A of the tube clamp release lever 502 with the fingers in the PR-direction against force of the second spring 505, centering the supporting portion 502C, the roller 502R abuts an abutting portion 501H of the tube clamp member 501 and lifts up the abutting portion 501H. Accordingly, the tube clamp member 501 is configured to rotate in the FR-direction to be lifted up against the force of the first spring 504.

Further, a configuration of the clip clamp member 503 illustrated in FIG. 7A will be described. As illustrated in FIG. 7A, the clip clamp member 503 has a function to detachably clamp the clip member 510 which the medical staff has attached inside the space SSP. The clip clamp member 503 includes an operation end portion 503A and a supporting portion 503C. The operation end portion 503A is one end portion of the clip clamp member 503, and the supporting portion 503C is the other end portion of the clip clamp member 503. The supporting portion 503C includes the tubular portion where the shaft portion 508A is passed though, although not illustrated. In other words, the tube clamp member 501 and the clip clamp member 503 are configured to be rotatable around the shaft portion 508A concentrically in the FR-direction.

As illustrated in FIG. 7A, since the clip clamp member 503 is disposed next on the right side of the tube clamp member 501, the right side surface portion 501S of the tube clamp member 501 contacts a left side surface portion 503S of the clip clamp member 503. An engaging projection 501M is formed on the right side surface portion 501S of the tube clamp member 501, and an engaging recess 503M is formed on the left side surface portion 503S of the clip clamp member 503. The engaging projection 501M is engaged with the engaging recess 503M. The engaging projection 501M and the engaging recess 503M form an engagement section 579.

With this configuration, when the tube clamp member 501 is lowered in the Z1-direction (PR-direction), the clip clamp member 503 can be also lowered in the Z1-direction (PR-direction) together with the tube clamp member 501 at the same time. In contrast, when the tube clamp member 501 is lifted up in the Z2-direction (FR-direction), the clip clamp member 503 is not lifted up in the Z2-direction (FR-direction) and the clip clamp member 503 is released from restriction of the tube clamp member 501.

Next, a configuration of the clip member 510 will be described with reference to FIGS. 8A and 8B. FIG. 8A is a diagram illustrating a left side surface of the clip member 510 (downstream side surface), and FIG. 8B is a diagram illustrating a right side surface of the clip member 510 (upstream side surface).

As it has been already described, the clip member 510 is preliminarily attached to the middle portion of the infusion tube 200, and the clip member 510 is detachably attached inside the space SSP of the tube clamp mechanism 500 in the state illustrated in FIGS. 6A, 7A and 7B. Accordingly, the clip member 510 blocks the middle portion of the infusion tube 200 and forms a blocking portion 200S.

However, in the different state illustrated in FIG. 6B, the clip member 510 is not preliminarily attached to the middle portion of the infusion tube 200. Therefore, the clip member 510 is not attached to the space SSP of the tube clamp mechanism 500. In other words, this is the case where the medical staff forgets to preliminarily attach the clip member 510 to the middle portion of the infusion tube 200, for example.

As illustrated in FIGS. 8A and 8B, the clip member 510 can be attached inside the space SSP by the medical staff inserting the clip member 510 into the space SSP in a Y1-direction, and the clip member 510 is clamped and held by the clip clamp member 503. Also, the clip member 510 can be detached by the medical staff pulling out the clip member 510 from the space SSP in a Y2-direction as illustrated in FIGS. 8A and 8B. The space SSP is the lower portion of the clip clamp member 503, and formed on the right side of the tube clamp release lever 502.

As illustrated in FIGS. 6A and 6B, receiving portions 519, 521 are formed at the lower portion 2B of the main body 2 in a protruding manner. The receiving portions 519, 521 and the clip clamp member 503 are configured to receive and hold the lower side, left side, and upper side, respectively, of the clip member 510 inserted into the space SSP. Further, for example, a guide groove 520 having a substantially semicircular shape or the like is formed along the X-direction at the lower portion 2B of the main body 2 in order to surely guide the infusion tube 200. The guide groove 520 is formed along the X-direction between the tube clamp member 501, the receiving portion 521 and the second infusion tube holding unit 55, and can surely hold the position of the infusion tube 200 with respect to the tube clamp mechanism 500.

Referring back to FIGS. 8A and 8B, the clip member 510 includes a fixing portion 511 on a lower portion side and a movable portion 512 on an upper portion side. The fixing portion 511 includes a front end portion 511A, a rear end portion 511B, and a tube blocking section 511C. The tube blocking section 511C is formed between the front end portion 511A and the rear end portion 511B. The front end portion 511A is a gripping portion that the medical staff grips with the fingers, and the rear end portion 511B is an inserting end portion into which the clip member 510 is inserted in the Y1-direction.

The movable portion 512 illustrated in FIGS. 8A and 8B includes a front end portion 512A, a rear end portion 512B, and a tube blocking section 512C. The tube blocking section 512C of the movable portion 512 is formed between the front end portion 512A and the rear end portion 512B. The front end portion 512A is a gripping portion that the medical staff grips with the fingers. The rear end portion 512B of the movable portion 512 is continuously formed from the rear end portion 511B of the fixing portion 511, and the front end portion 512A of the movable portion 512 can be rotatably moved in the FR-direction by elastic force of the movable portion 512, centering the rear end portion 512B of the movable portion 512.

The tube blocking section 511C and the tube blocking section 512C illustrated in FIGS. 8A and 8B face each other, and the middle portion of the infusion tube 200 is preliminarily and detachably passed between the tube blocking section 511C and the tube blocking section 512C. As illustrated in FIG. 8A, when the movable portion 512 is opened to the fixing portion 511 to expand a space between the tube blocking section 511C and the tube blocking section 512C, the middle portion of the infusion tube 200 is prevented from being squeezed. On the other hand, when the movable portion 512 is closed to the fixing portion 511 to narrow the space between the tube blocking section 511C and the tube blocking section 512C as illustrated in FIGS. 8A and 8B, the middle portion of the infusion tube 200 is squeezed by forming the blocking portion 200S. As a result, the medicine is inhibited from flowing through the infusion tube 200.

Next, exemplary operation of the tube clamp mechanism 500 in FIGS. 7A and 7B will be described with reference to FIGS. 9 to 14. When the infusion tube 200 is set at the tube attachment section 50 of the infusion pump 1 in the X-direction (horizontal direction) with the access cover 5 opened as illustrated in FIG. 4, the tube clamp mechanism 500 in FIGS. 7A and 7B inhibits the medicine from freely flowing through the infusion tube 200. However, while the access cover 5 is closed, the tube clamp mechanism 500 in FIGS. 7A and 7B can feed the medicine in the T-direction through the infusion tube 200. In the following, exemplary operation of the tube clamp mechanism 500 will be described. Note that the clip member 510 is preliminarily attached to the middle portion of the infusion tube 200 as illustrated in FIG. 5.

FIGS. 9A and 9B is a diagram illustrating a state in which the access cover 5 is already opened, and the medical staff has pushed down the tube clamp release lever 502 of the tube clamp mechanism 500 to lift up the tube clamp member 501 along the FR-direction.

As illustrated in FIG. 9A, the access cover 5 is already opened and the operation end portion 502A of the tube clamp release lever 502 is lifted up although the operation end portion 501A of the tube clamp member 501 and the operation end portion 503A of the clip clamp member 503 adjacent to the tube clamp member 501 are lowered to a substantially horizontal state. In other words, since the tube clamp member 501, the clip clamp member 503 adjacent to the tube clamp member 501, and the tube clamp release lever 502 are positioned close to each other, the tube clamp mechanism 500 is in a closed state.

As illustrated in FIG. 9B, when the medical staff pushes down the operation end portion 502A of the tube clamp release lever 502 in the PR-direction against the force of the second spring 505 illustrated in FIGS. 7A and 7B, the operation end portion 501A of the tube clamp member 501 is lifted up in the FR-direction against force of the first spring 504. When the operation end portion 501A of the tube clamp member 501 is lifted up in the FR-direction as described above, the adjacent operation end portion 503A of the clip clamp member 503 is not lifted up together with the operation end portion 501A of the tube clamp member 501 and kept in the horizontal state same as a state illustrated in FIG. 9A. However, the clip clamp member 503 is released from the tube clamp member 501 and becomes a free state in which the clip clamp member 503 can be freely lifted up in the FR-direction.

FIG. 10A is a diagram illustrating a state in which the access cover 5 is opened and the medicine is inhibited from flowing through the infusion tube 200 by forming the blocking portion 200S on the infusion tube 200 while the clip member 510 preliminarily attached to the infusion tube 200 is inserted to the space SSP of the tube clamp mechanism 500. FIG. 10B is a diagram illustrating a state in which the access cover 5 pushes and forcibly lifts up tube clamp member 501 when the medical staff closes the access cover 5 later.

The medical staff sets the infusion tube 200 preliminarily attached with the clip member 510 illustrated in FIG. 5 inside the guide groove 520 at the lower portion 2B of the main body 2 as illustrated in FIG. 10A and also attaches the clip member 510 inside the space SSP along the Y1-direction. Since the movable portion 512 of the clip member 510 is pressed down by the clip clamp member 503, the movable portion 512 is closed to fixing portion 511.

In this state, the space between the tube blocking section 511C and the tube blocking section 512C is narrowed as illustrated in FIGS. 8A and 10A. Accordingly, the tube blocking section 511C and the tube blocking section 512C form the blocking portion 200S at the middle portion of the infusion tube 200 by squeezing the middle portion of the infusion tube 200. The blocking portion 200S can block the medicine trying to flow through the infusion tube 200. Thus, even when the infusion tube 200 and the clip member 510 are set to the tube clamp mechanism 500 with the access cover 5 opened, the clip member 510 forms the blocking portion 200S on the infusion tube 200. Therefore, the medicine is prevented from flowing through the infusion tube 200.

Next, as illustrated in FIG. 10B, the medical staff rotates the access cover 5 in the CR-direction and closes the lower portion 2B of the main body 2 and the infusion tube 200. When the access cover 5 is closed in the CR-direction, the access cover 5 forcibly pushes up the operation end portion 501A of the tube clamp member 501 in the FR-direction against force of the first spring 504 illustrated in FIGS. 7A and 7B. When the operation end portion 501A of the tube clamp member 501 is forcibly pushed up in the FR-direction, the operation end portion 502A of the tube clamp release lever 502 is lifted up in the FR-direction by force of the second spring 505 and returns to an initial state illustrated in FIG. 9A.

At this point, according to an embodiment of the present invention, the tube clamp member 501 includes the biasing first spring 504, but the clip clamp member 503 does not include a biasing spring as illustrated in FIGS. 7A and 7B.

Considering a comparative example in which the biasing spring is provided in both the tube clamp member 501 and the clip clamp member 503, strong force is necessary when the access cover 5 pushes up both the tube clamp member 501 and the clip clamp member 503 against the force of the two springs along with the closing operation of the access cover 5 as illustrated in the changing states from FIG. 10A to FIG. 10B.

However, according to an embodiment of the present invention, the access cover 5 only has to push up the tube clamp member 501 against force of the first spring 504 of the tube clamp member 501. Therefore, the medical staff can close the access cover 5 with relatively small force because the closing operation is to be carried out only against the force of the one first spring 504. As a result, the access cover 5 can be easily closed.

FIG. 11A is a diagram illustrating a state in which the clip clamp member 503 is also lifted up together with lift-up of the tube clamp member 501 in the FR-direction when the medical staff closes the access cover 5. FIG. 11B is a diagram illustrating a state in which the clip member 510 is opened by the elastic force of the clip member 510 and releases pressure force to infusion tube 200 to eliminate the blocking portion 200S formed at the infusion tube 200, thereby allowing the medicinal solution to pass through the infusion tube 200.

In FIG. 11A, when the tube clamp member 501 illustrated in FIG. 7A is lifted up in the Z2-direction (corresponding to the FR-direction illustrated in FIG. 11A) while the access cover 5 is completely closed, the clip clamp member 503 is not lifted up together with the tube clamp member 501 in the Z2-direction (FR-direction) at the same time, and the tube clamp member 501 operates separately from the clip clamp member 503. Accordingly, rotation of the clip clamp member 503 is not restricted by the tube clamp member 501, and the clip clamp member 503 can freely rotate in the FR-direction. This is caused because the engaging projection 501M illustrated in FIG. 7A is disengaged from the engaging recess 503M, and the clip clamp member 503 is released from restriction by the tube clamp member 501 and the clip clamp member 503 can freely rotate in the FR-direction.

Since the clip clamp member 503 can thus freely rotate in the FR-direction with the access cover 5 completely closed, the front end portion 512A of the movable portion 512 of the clip member 510 opens in the FR-direction by the elastic deforming force of the movable portion 512 itself so as to separate from the front end portion 511A of the fixing portion 511 as illustrated in FIG. 11B. This expands the space between the front end portion 512A of the movable portion 512 of the clip member 510 and the front end portion 511A of the fixing portion 511 while the access cover 5 is closed. Therefore, the blocking portion 200S at the middle portion of the infusion tube 200 is eliminated. Since the blocking portion 200S is eliminated, the infusion tube 200 can feed the medicine.

Next, FIG. 12A is a diagram illustrating a state in which the clip member 510 is going to close the middle portion of the infusion tube 200 when the medical staff is going to open the access cover 5 after completion of predetermined medicine feeding.

Figure 13A:
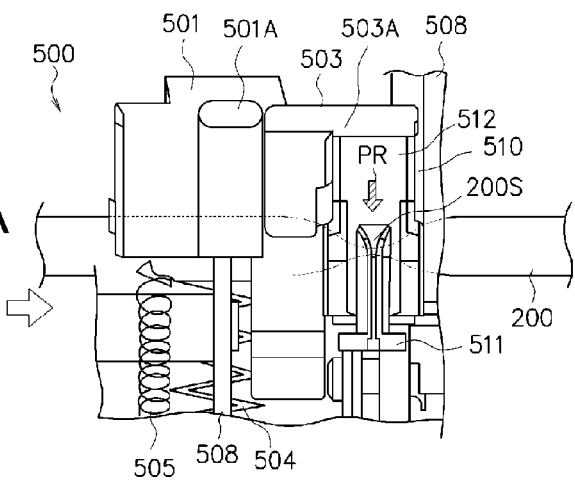
FIG. 13A is a front perspective diagram illustrating a state in which the blocking portion is formed at the infusion tube by closing the clip member and inhibits the medicine from passing through the infusion tube while the access cover is opened.
Figure 13B:
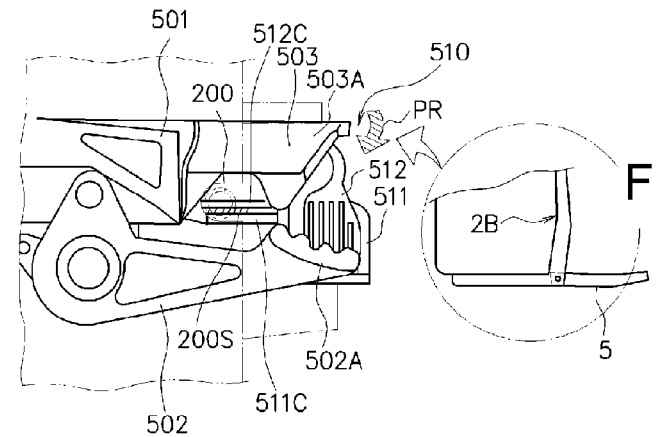
FIG. 13B is a left side perspective view of the state shown in FIG. 13A.
Figure 13C:
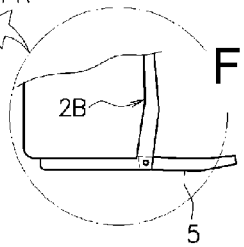
FIG. 13C is a diagram illustrating the position of the access cover related to the position of the mechanism in FIGS. 13A and 13B.

In the case where the medical staff opens the access cover 5 in the CS-direction after completion of the medicine feeding as illustrated in FIG. 12A, it is possible to release the state in which the access cover 5 forcibly pushes up the operation end portion 501A of the tube clamp member 501 as illustrated in FIG. 12A. Therefore, the tube clamp member 501 rotates and returns in the PR-direction by force of the first spring 504 illustrated in FIGS. 7A and 7B. When the tube clamp member 501 thus returns in the PR-direction, the operation end portion 503A of the clip clamp member 503 is also simultaneously pushed down in the PR-direction by the force of the first spring 504 as illustrated in FIGS. 13A and 13B.

Therefore, since the operation end portion 503A of the clip clamp member 503 forcibly pushes down the movable portion 512 of the clip member 510 in the PR-direction by force of the first spring 504 in FIGS. 7A and 7B, the front end portion 512A of the movable portion 512 of the clip member 510 is closed toward the front end portion 511A of the fixing portion 511 in the PR-direction against the elastic force of the movable portion 512 itself.

This narrows the space between the front end portion 512A of the movable portion 512 of the clip member 510 and the front end portion 511A of the fixing portion 511, thereby squeezing the middle portion of the infusion tube 200 to form the blocking portion 200S. Accordingly, infusion tube 200 cannot feed the medicine. In other words, the infusion pump 1 in FIG. 1 can inhibit feeding by use of the infusion tube 200.

As described above, when the medical staff closes the access cover 5, the infusion pump 1 in FIG. 1 can feed the medicinal solution through the infusion tube 200 without blocking the infusion tube 200. Further, when the medical staff opens the access cover 5 after completion of medicinal solution feeding, the medicinal solution can be surely inhibited from feeding by blocking the middle portion of the infusion tube 200 at the infusion pump 1.

Figures 14A, 14C:
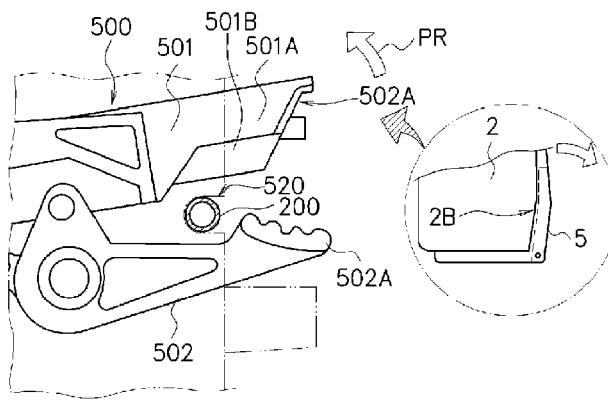
FIG. 14A is a diagram illustrating the clamp mechanism without a clip member in a state in which the blocking portion at the infusion tube is eliminated and the medicinal solution passes through the infusion tube.
FIG. 14C is a diagram illustrating the position of the access cover related to the position of the mechanism in FIG. 14A.
Figures 14B, 14D:
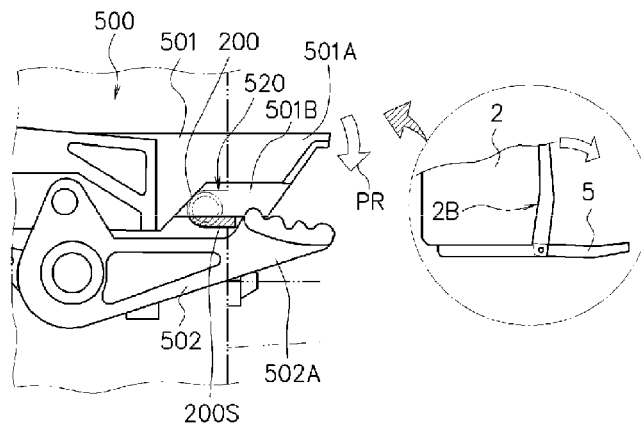
FIG. 14B is a diagram illustrating a state in which the tube clamp mechanism inhibits the medicine from passing through the infusion tube by forming the blocking portion at the infusion tube even in the case where the clip member is not preliminarily attached to the infusion tube.
FIG. 14D is a diagram illustrating the position of the access cover related to the position of the mechanism in FIG. 14B.

Next, description will be given by reference to FIGS. 14A and 14B. FIGS. 14A and 14B are diagrams illustrating that the tube clamp mechanism 500 forms the blocking portion 200S at the middle portion of the infusion tube 200 and can inhibit the medicine from passing through the infusion tube 200 even in the case where the clip member 510 is not preliminarily attached to the infusion tube 200. As illustrated in FIG. 5, description will be given for a case in which the medical staff unintentionally attaches the infusion tube 200 unattached with the clip member 510 to the lower portion 2B of the main body 2 even though the clip member 510 is not preliminarily attached to the middle portion of the infusion tube 200 for some reason, different from the case where the clip member 510 is preliminarily attached to the middle portion of the infusion tube 200.

FIG. 14A is a diagram illustrating a state in which the infusion tube 200 is attached and the access cover 5 is completely closed. While the access cover 5 is closed, the tube clamp member 501 is pushed up in the FR-direction by the access cover 5 against force of the first spring 504 illustrated in FIGS. 7A and 7B. Therefore, the tube blocking section 501B of the tube clamp member 501 is separated from the middle portion of the infusion tube 200. Accordingly, the middle portion of the infusion tube 200 is not squeezed. Therefore, the infusion tube 200 can feed the medicine.

On the other hand, when the medical staff opens the access cover 5 from the closed state of the access cover 5 as illustrated in FIG. 14B, the tube clamp member 501 is released from being pushed by the access cover 5. Therefore, the tube clamp member 501 is pushed back in the PR-direction by force of the first spring 504. In this manner, the tube blocking section 501B of the tube clamp member 501 squeezes the middle portion of the infusion tube 200 and forms the blocking portion 200S. As a result, despite the fact that the clip member 510 is not preliminarily attached to the middle portion of the infusion tube 200, the tube blocking section 501B of the tube clamp member 501 surely squeezes the infusion tube 200 and forms the blocking portion 200S when the medical staff opens the access cover 5. Therefore, the medicine trying to flow through the infusion tube 200 can be surely blocked. When the access cover 5 is thus opened, the medicine is prevented from flowing through the infusion tube 200 even in the case where the clip member 510 is not attached to the infusion tube 200.

As illustrated in FIGS. 7A and 7B, the infusion pump 1 according to an embodiment of the present invention includes the tube attachment section 50 where the infusion tube 200 is detachably attached in the horizontal direction, the access cover 5 that can close the tube attachment section 50 in an openable manner, and the tube clamp mechanism 500 disposed at the tube attachment section 50 and configured to clamp and block the middle portion of the infusion tube 200.

When the access cover 5 is opened, the tube clamp mechanism 500 closes the clip member 510 preliminarily attached at the middle portion of the infusion tube 200 and forms blocking portion 200S on the infusion tube 200 by the clip member 510, and when the access cover 5 is closed, the tube clamp mechanism 500 opens the clip member 510 and eliminates the blocking portion 200S formed at the infusion tube 200. Thus, when the access cover 5 is opened, the tube clamp mechanism 500 disposed at the tube attachment section 50 closes the clip member 510 preliminarily attached to the middle portion of the infusion tube 200 and forms the blocking portion 200S at the infusion tube 200 by the clip member 510, and when the access cover 5 is closed, the tube clamp mechanism 500 opens the clip member 510 and eliminates the blocking portion 200S formed at the infusion tube 200. With this configuration, in the case where the access cover 5 is still opened even after the infusion tube 200 is attached to the infusion pump 1, the medicine is prevented from freely flowing through the infusion tube 200, and in the case where the access cover 5 is closed, the medicinal solution can be passed through the infusion tube 200, thereby achieving to feed the medicinal solution safely.

The tube clamp mechanism 500 includes the base member 506, clip clamp member 503, tube clamp member 501, and tube clamp release lever 502. The clip clamp member 503 is rotatably mounted on the base member 506 and clamps the clip member 510. In the case where access cover 5 is opened, the clip clamp member closes the clip member 510, thereby forming the blocking portion 200S at the infusion tube 200. The tube clamp member 501 is rotatably mounted on the base member 506. In the case where the access cover 5 is opened, the blocking portion 200S is formed at the infusion tube 200 by pushing the clip clamp member 503 and closing the clip member 510, and in the case where the access cover 5 is closed, the blocking portion 200S formed at the infusion tube 200 is eliminated by opening the clip member 510 because pushing operation to the clip clamp member 503 is released by being pushed by the access cover 5. The tube clamp release lever 502 is rotatably mounted on the base member 506. When the tube clamp release lever 502 is pushed by a user, the clip clamp member 503 is made to clamp the clip member 510 by pushing up the tube clamp member 501 in a direction away from the infusion tube 200 to achieve to push up the clip clamp member 503. With this configuration, the blocking portion 200S can be formed at the infusion tube 200 by closing the clip member 510 if only provided with the tube clamp member 501, clip clamp member 503, and tube clamp release lever 502. Therefore, the medicine can be prevented from freely flowing through the infusion tube 200 in the case where the access cover 5 is still opened even though the infusion tube 200 is attached to the infusion pump 1.

The tube clamp member 501 forms the blocking portion 200S by pressing the middle portion of the infusion tube 200 in the case where the access cover 5 is opened when the clip member 510 is not preliminarily attached to the middle portion of the infusion tube 200. When the access cover 5 is closed, the tube clamp member 501 eliminates the blocking portion 200S by separating itself from the infusion tube 200. With this configuration, even in the case where the clip member 510 is not preliminarily attached to the middle portion of the infusion tube 200, for example, in the case where the user forgets to preliminarily attach the clip member 510 to the middle portion of the infusion tube 200, the blocking portion 200S can be formed by pressing the middle portion of the infusion tube 200 in the case where the access cover 5 is opened. Therefore, in the case where the access cover 5 is opened, the medicine can be prevented from freely flowing through the infusion tube 200.

The engagement section 579 illustrated in FIGS. 7A and 7B engages the tube clamp member 501 with the clip clamp member 503 so as to be integrally rotated in the case of operating in a direction close to the infusion tube 200, and disengages the tube clamp member 501 from the clip clamp member 503 to release the clip clamp member 503 from restriction of the tube clamp member 501 in the case of operating in a direction away from the infusion tube 200. With this configuration, the engagement section disengages the tube clamp member 501 from the clip clamp member 503 and can release the clip clamp member 503 from restriction of the tube clamp member 501 in the case of operating in the direction away from the infusion tube 200. Therefore, the clip member 510 can be easily attached and clamped to the clip clamp member 503.

Additionally, the spring 504 for biasing the tube clamp member 501 toward the infusion tube 200 is provided, and the tube clamp member 501 is separated from the infusion tube 200 against force of the spring 504 when the tube clamp release lever 502 is pushed by the user. With this configuration, when the tube clamp release lever 502 is pushed by the user, the tube clamp member 501 is separated from the infusion tube 200 against force of the spring 504, thereby disengaging the tube clamp member 501 from the clip clamp member 503 and achieving to release the clip clamp member 503 from restriction of the tube clamp member 501. Accordingly, the clip member 510 can be easily attached and clamped to the clip clamp member 503 without being affected by the tube clamp member 501 biased toward the infusion tube 200.

The display unit 3 that displays information, and the operation panel 4 including operating buttons are disposed at the upper portion of the main body of the infusion pump 1, and the tube attachment section 50 and the access cover 5 are disposed at the lower portion of the main body of the infusion pump 1. With this configuration, the medical staff can feed the medicinal solution, confirming the information of the display unit 3 at the upper portion of the main body, and further can operate the operating button at the operation panel 4, confirming the information of the display unit 3 at the upper portion of the main body. The infusion tube 200 can be attached by opening the access cover 5 at the lower portion of the main body.

Note that the present invention is not limited to the above-described embodiment, and various modifications can be made without departing from the scope of the following claims. As illustrated in FIG. 2, the infusion tube 200 is horizontally disposed at the tube attachment section 50 and the right side is the upstream side of the medicinal solution and the left side is the downstream side of the medicinal solution when a person faces the tube attachment section. However, not limited thereto, the infusion tube 200 may also be disposed in a slightly tilting manner such that the upstream side becomes slightly higher than the downstream side although being horizontal at tube attachment section 50. According to an embodiment of the present invention, the horizontal direction in which infusion tube 200 is disposed includes the horizontal direction and the direction slightly tilted from the horizontal direction.

The respective components recited in the above-described embodiment may be partly omitted or suitably combined in a manner different from above.

What is claimed is:

1. An infusion pump comprising:
    a tube attachment section configured such that an infusion tube is detachably attachable to the tube attachment section;
    an access cover configured to close the tube attachment section in an openable manner;
    a tube clamp mechanism located within the tube attachment section and configured to clamp and block a portion of the infusion tube, the tube clamp mechanism comprising:
        a base member,
        a clip clamp member rotatably mounted on the base member,
        a tube clamp release lever rotatably mounted on the base member, and
        a tube clamp member rotatably mounted on the base member; and
    an engagement section configured to engage the tube clamp member with the clip clamp member,
    wherein the clip clamp member is configured to reversibly clamp a clip member that is attachable to a portion of the infusion tube, such that when the access cover is open and the clip member is present, the clip clamp member clamps the clip member and thereby forms a blocking portion at a location along the infusion tube, and such that when the access cover is closed and the clip member is present, the clip clamp member releases the clip member and thereby eliminates the blocking portion,
    wherein the tube clamp release lever is configured to push the tube clamp member in a direction away from the infusion tube when the tube clamp release lever is pushed by a user, and
    wherein the engagement section, the tube clamp member, and the clip clamp member are configured such that, when the access cover changes from an open position to a closed position, the engagement section engages the tube clamp member with the clip clamp member such that the tube clamp member and the clip clamp member are integrally rotated.

2. The infusion pump according to claim 1, wherein the tube clamp member is configured to clamp a portion of the infusion tube and form a second blocking portion when the clip member is not present and the access cover is open, and to separate from the infusion tube and eliminate the second blocking portion when the access cover is closed.

3. The infusion pump according to claim 1, wherein the engagement section, the tube clamp member, and the clip clamp member are configured such that, when the access cover changes from the closed position to the open position, the engagement section disengages the tube clamp member from the clip clamp member.

4. The infusion pump according to claim 1, further comprising a first spring configured to bias the tube clamp member to clamp the infusion tube.

5. The infusion pump according to claim 4, further comprising a second spring attached at a first end to the tube clamp release lever and at a second end to the base member.

6. The infusion pump according to claim 5, wherein a spring constant of the second spring is 3 to 8 percent of a spring constant of the first spring.

7. The infusion pump according to claim 1, further comprising a display unit disposed on an upper portion of the infusion pump and configured to display information.

8. The infusion pump according to claim 1, further comprising an operation panel provided with operating buttons disposed on an upper portion of the infusion pump.

9. The infusion pump according to claim 1, wherein the tube attachment section and the access cover are disposed on a lower portion of the infusion pump.

10. The infusion pump according to claim 1, further comprising the clip member.

11. The infusion pump according to claim 1, further comprising a liquid feed driving unit.

12. The infusion pump according to claim 11, further comprising an infusion tube pressing member disposed on the access cover.

13. The infusion pump according to claim 1, wherein the infusion pump is configured to have the infusion tube attached to be held in a horizontal orientation.

14. The infusion pump according to claim 1, further comprising a bubble sensor, an upstream block sensor, and a downstream block sensor disposed in the tube attachment section.

15. The infusion pump according to claim 1, wherein the tube clamp member, the tube clamp release lever, and the clip clamp member are made of plastic material.

16. An infusion pump comprising:
a tube attachment section configured such that an infusion tube is detachably attachable to the tube attachment section;
an access cover configured to close the tube attachment section in an openable manner; and
a tube clamp mechanism located within the tube attachment section and configured to clamp and block a portion of the infusion tube,
the tube clamp mechanism comprising:
a base member;
a clip clamp member rotatably mounted on the base member;
a tube clamp release lever rotatably mounted on the base member; and
a tube clamp member rotatably mounted on the base member, wherein the clip clamp member is configured to reversibly clamp a clip member that is attachable to a portion of the infusion tube, such that when the access cover is open and the clip member is present, the clip clamp member clamps the clip member and thereby forms a blocking portion at a location along the infusion tube, and such that when the access cover is closed and the clip member is present, the clip clamp member releases the clip member and thereby eliminates the blocking portion, and wherein the tube clamp release lever is configured to push the tube clamp member in a direction away from the infusion tube when the tube clamp release lever is pushed by a user;
the infusion pump further comprising an engagement section configured to engage the tube clamp member with the clip clamp member so as to be integrally rotated in a case of operating in a direction toward the infusion tube, and disengage the tube clamp member from the clip clamp member to release the clip clamp member from restriction of the tube clamp member in a case of operating in a direction away from the infusion tube.

* * * * *